United States Patent [19]

Lenz et al.

[11] 4,265,247

[45] May 5, 1981

[54] MALIC ACID POLYMERS

[75] Inventors: Robert W. Lenz, Amherst, Mass.; Michel Vert, Deville-les-Rouen, France

[73] Assignee: Research Corporation, New York, N.Y.

[21] Appl. No.: 92,183

[22] Filed: Nov. 7, 1979

[51] Int. Cl.³ .................... C08G 63/08; A61L 17/00
[52] U.S. Cl. .................... 128/335.5; 528/323; 528/359; 528/361
[58] Field of Search .............. 528/323, 359, 361; 128/335.5

[56] References Cited

U.S. PATENT DOCUMENTS

| 3,268,486 | 8/1966 | Klootwijk | 260/78.3 |
| 3,287,325 | 11/1966 | Williams | 260/78.3 |
| 3,471,454 | 10/1969 | Blume | 260/78.3 |

*Primary Examiner*—Earl A. Nielsen

*Attorney, Agent, or Firm*—Oblon, Fisher, Spivak, McClelland & Maier

[57] ABSTRACT

A polymer containing repeating units of the formula:

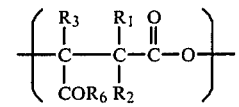

wherein $R_1$ and $R_2$ are independently hydrogen, alkyl, aryl, aralkyl, substituted alkyl, substituted aryl, substituted aralkyl, $R_3$ is hydrogen, alkyl or $-(CH_2)_n COOR_8$ where n is an integer of 0 to 10, $R_6$ is OR or $NR_4R_5$, wherein R and $R_8$ are independently hydrogen or a group derived from a compound containing esterifiable hydroxyl groups, $R_4$ and $R_5$ are independently alkyl, aryl, aralkyl, substituted alkyl, substituted aryl, substituted aralkyl or together comprise an alkylene group.

16 Claims, No Drawings

MALIC ACID POLYMERS

BACKGROUND OF THE INVENTION

1. Field of the Invention

The present invention is directed to polymers prepared from β-malolactone or its derivatives.

2. Description of the Prior Art

In recent years there has been an increase in the interest in the use of synthetic polymers for biomedical and pharmacological applications in particular as absorbable suture material, drug carriers for slow release medication and the like. It has been suggested in the prior art to manufacture synthetic absorbable sutures from polyesters of hydroxycarboxylic acids, notably polylactide, polyglycolide and copolymers of lactide and glycolide. Such synthetic suture materials are described in U.S. Pat. Nos. 3,636,956 and 3,297,033.

There exists a need, however, for polymeric materials which not only may be degraded, but wherein the low molecular weight residues can be metabolized by normal metabolic pathways. Additionally, there exists a need for synthetic materials to which drugs may be bonded to provide for a local application of the drug and/or slow release of the drug to the body. In addition, it is highly desirable that such synthetic polymers be prepared from naturally occurring materials in view of the greatly increased cost of petrochemicals.

SUMMARY OF THE INVENTION

Accordingly, it is an object of the present invention to prepare polymers containing pendant carboxyl groups.

It is an additional object of the present invention to produce synthetic polymers from naturally occurring substances.

It is a further object of the present invention to develop synthetic polymers which degrade in the human body and whose degradation products may be eliminated by the normal metabolic pathways.

It is still a further object of the present invention to provide for synthetic polymers which can act as drug carriers for localized applications or slow release of drugs to the body.

These and other objectives of the present invention have been attained through the preparation of polymers of malic acid and its derivatives.

DESCRIPTION OF THE PREFERRED EMBODIMENTS

The polymers of the present invention are obtained by polymerizing lactones of the formula:

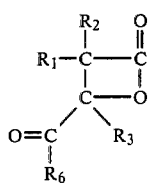
(I)

wherein $R_1$ and $R_2$ each may be hydrogen, alkyl, aryl, aralkyl, substituted alkyl, substituted aryl, substituted aralkyl or the like; $R_3$ is hydrogen, lower alkyl, or $-(CH_2)_n-COOR_8$ where n is an integer of 1 to 10 or 0, preferably from 1 to 6; $R_6$ is OR, $NR_4R_5$ or anions, wherein R and $R_8$ are independently a hydrogen or a group derived from a compound containing esterifiable hydroxyl groups, for instance alcohols, preferably $C_1-C_6$ alcohols, more preferably methanol or ethanol or benzylalcohol, aromatic alcohols such as phenols, or may be a radical from a pharmaceutical which can be hydrolyzed to the active drug, a radical from an agricultural chemical such as a herbicide, fungicide, bacteriocide or fertilizer which may be hydrolyzed to release the active chemical, or it may be a radical from a cosmetic which may be hydrolyzed to the free cosmetic. In this manner such chemicals may be converted into slow release compositions. $R_4$ and $R_5$ may be alkyl, aryl, aralkyl, or together may comprise an alkylene group containing from 3 to 7 carbon atoms. Preferred alkyl groups in the above definition are the $C_1-C_5$ lower alkyl groups. Preferred aryl is phenyl. Preferred aralkyl is benzyl. These groups can be substituted with other lower alkyl groups, chloro, bromo, fluoro, cyano, nitro or

groups wherein $R_9$ and $R_{10}$ are each hydrogen or lower alkyl.

The lactones wherein $R_1$, $R_2$ and $R_3$ are hydrogen may be derived from malic acid by esterification or amidation reaction. Lactones wherein $R_3$ is methyl and $R_1$ and $R_2$ are hydrogen may be prepared from naturally occurring citramalic acid while lactones wherein $R_1$ and $R_2$ are hydrogen and $R_3$ is methylene carboxy methyl or similar ester or amide group, may be prepared from citric acid. Alternative methods of preparing these compounds may be found in U.S. Pat. Nos. 2,444,735 and 2,456,503 to Hagemeyer. In addition, such lactones may be prepared from the β-halo derivative of dicarboxylic acids.

The β-lactones can be readily polymerized by either anionic or cationic mechanisms, depending upon the substituents on the lactone ring according to the following reaction scheme:

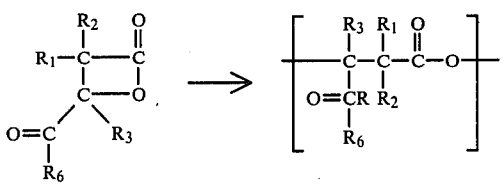

The polymer may have as terminal groups

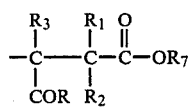

wherein R, $R_1$, $R_2$ and $R_3$ are as defined previously and $R_7$ is hydrogen, a group derived from a compound containing esterifiable hydroxyl groups including $C_1-C_6$ alcohols, phenols or the like.

When $R_3$ is hydrogen, either acid or basic conditions may be employed for the polymerization process. When $R_3$ is other than hydrogen, acidic conditions are preferably employed to obtain higher molecular weight polymers. If the free carboxyl group is desired, then the ester or amide groups in the polymer are simply converted into free carboxylic acid groups using conventional techniques.

In addition to the preparation of homopolymers, copolymers, terpolymers or the like of malic acid or its derivatives may be prepared. For example, a mixture of the lactones of Formula (I) containing both ester and amide groups may be employed to produce a polymer. In addition, it is possible to prepare copolymers containing both ester and free acid groups, amide and free acid groups, or a combination of ester, amide and free acid groups. The free acid groups are introduced into the polymer chain by conversion of the ester and/or amide groups. The number of free acid groups may be readily controlled by use of appropriate reaction conditions as is readily apparent.

In addition, copolymers with other lactones, cyclic esters, lactams or cyclic amides containing up to 5, 6 or 7 members in the ring may also be prepared. Suitable lactones or cyclic esters which may be copolymerized with the malolactones of the present invention include pivalolactone, caprolactone, $\beta$-propiolactone, tetramethylglycolide, $\beta$-butyrolactone, $\gamma$-butyrolactone, intramolecular cyclic esters of $\alpha$-hydroxybutyric acid, $\alpha$-hydroxyisobutyric acid, $\alpha$-hydroxyvaleric acid, $\alpha$-hydroxyisovaleric acid, $\alpha$-hydroxyethylbutyric acid, $\alpha$-hydroxycaproic acid, $\alpha$-hydroxy-$\beta$-methylvaleric acid, $\alpha$-hydroxyisocaproic acid, $\alpha$-hydroxyheptanoic acid, $\alpha$-hydroxyoctanoic acid, $\alpha$-hydroxydecanoic acid, $\alpha$-hydroxymyristic acid, $\alpha$-hydroxystearic acid, $\alpha$-hydroxylignoceric acid and the like, glycolide and lactolide. Lactam and cyclic amides such as caprolactam, $\beta$-propiolactam, aminoacid anhydride and the like may be used as comonomers. In addition, epoxides such as ethylene oxide and propylene oxide as well as cyclic ethers such as trioxane and oxetanes may also be copolymerized with the lactones of the present invention. Such copolymers, terpolymers or the like may be prepared by copolymerizing from 5 to 95 mole % preferably from 10 to 50 mole % of the malolactone derivative with another comonomer or comonomers. Copolymers with 5 to 25 mole % of caprolactam result in a nylon which is more readily dyable because of the pendant carboxyl groups.

The stereoregularity of the polymers of the present invention may be regulated as desired. A substantially amorphorous polymer may be obtained by polymerizing a racemic mixture of the malolactone ester or amide. On the other hand, a more stereoregular polymer would be obtained by polymerizing either the D or L malolactone ester or amide. If it is desired to produce compounds of intermediate stereoregularity, mixtures of the D and L malolactone ester or amide can be employed wherein the ratio of the D to L isomer is varied. Furthermore, the use of a polymerization catalyst which causes stereospecific polymerization of the racemic monomer mixture, such as trialkylaluminum compounds, can also be used to produce a polymer having the desired degree of stereoregularity.

$\beta$-lactones in general are known to polymerize by both anionic and cationic mechanisms depending upon the substituent on the lactone ring. In general, however, $\beta$-substituted-$\beta$-lactones polymerize only by cationic reactions with acid catalysts, presumably because of steric hinderance by substituents at the $\beta$-position. That is, the anionic polymerization reaction of $\beta$-lactones occurs predominantly, if not entirely, by ring opening of the alkyl-oxygen bond through nucleophilic attack at the $\beta$-position. Nevertheless, it has now been found that when $R_3$ in the foregoing formula (I) is hydrogen, anionic initiators can be used to polymerize the $\beta$-lactone esters and amides. When employing anionic initiators it has been found that the molecular weight of the polymer produced is somewhat narrower than those obtained through the use of acid catalysts, and anionic initiators generally allow for more precise control over the molecular weight of the polymer produced.

The polymers of the present invention have a wide field of applicability. One use for these polymers and copolymers is in the preparation of degradable sutures. The polymers of the present invention degrade to malic acid which can be eliminated from the body via the normal metabolic pathways. In addition, the polymers of the present invention can be fabricated into bandages for wounds, burns, or the like. If desired, the polymers may have bound thereto medication for topical application to the wound. For example, antibiotics may be firmly bound to the polymers of the present invention and fabricated into a dressing for a wound. As the polymers degrade, the antibiotic is released into the wound site. The medication could be an antibiotic designed to prevent or treat infection at the wound site or could be medication designed to aid in the treatment of the wound. For instance, enzymes used in burn debridement may be bonded to these polymers.

The carboxyl groups on the polymers of the present invention can be converted into polyanions which have been recognized as having biomedical applications, see S. D. Bruck, *Polymer Reprints,* 19, No. 2, 220, 1978. Thus, the polymers of the present invention provide a method of administering such polyanions to the human body. The present polymers also may be used in slow release medication and for topical applications of medication. The particular drug to be administered is firmly bonded to the polymer through the pendant carboxyl groups. For slow release, the polymer containing the medication may be ingested orally or injected directly into the blood stream whereby the normal metabolic or hydrolytic processes of the body will cause the polymer to degrade and release the drug into the system. Alternatively, the polymer is implanted in the body whereby it slowly dissolves releasing the medication into the body stream. For all the ingested or implanted systems the release rate may be varied by altering the water swellability of the polymer through regulation of either the composition or the stereoregularity of the polymer. The former is done by blocking the free carboxyl groups with esters or amides or the like, or by similar known techniques. Local application of the drugs is achieved by implanting the polymer containing the drug at the desired site of drug application. For example, prostaglandins can be administered by bonding them to the polymer of the present invention and then implanting this material in the uterus. In this manner, prostaglandin material is released at the desired site. Similarly, antibiotics may be administered to the site of an infection by bonding them to the polymer of the present invention and then implanting this material at the site of the infection. For injection applications, the polymer may be rendered water soluble by adjusting the free carboxylic acid content of the polymer. The molecular weight of the polymer so injected is preferably in the range of 20,000 to 60,000 (number average).

In implantation or injection techniques the release rate of the drug is directly correlated to the water swellability of the polymers. The water swellability and solubility of the polymers can be altered by controlling the stereoregularity which decreases or increases the crystallinity of the polymers, and by the presence or absence of free carboxyl groups on the polymer. The more free carboxyl groups which are present, the greater the swellability of the polymer which in turn means the faster the polymer will degrade and the drug will be released. The greater the degree of crystallinity in the polymer, the less it will be swollen by body fluids and its rate of degradation will also be slower than for polymers of lesser degrees of crystallinity. Because of its lower rate swellability and lower rate of degradation, the lower the rate of drug release will be with increasing crystallinity. A combination of controlled crystallinity and controlled number of free carboxyl groups can be used to achieve the desired release rate. In addition, by using an admixture of polymers having different degrees of swellability and degradation rates, it is possible to achieve a release of drugs into the body system over a great period of time. For example, by bonding the drug to be delivered to a mixture of polymers having different degrees of crystallinity or different levels of free carboxyl groups, or a combination thereof, it is possible to fabricate a device which will release a drug into the body system over a long period of time. The medication bonded to that portion of the device fabricated from polymers having a rapid rate of degradation would be released comparatively quickly, while that bonded to the polymers which degraded more slowly would be released over longer periods in time.

Alternative methods of manufacturing slow release medications involve encapsulation of the medicine in capsules prepared from polymers of the present invention. By employing a mixture of capsules each having a different water swellability and rate of degradation, it is possible to produce slow release medication which is released over a long period of time at a consistent rate.

Biodegradable packaging may be prepared from the polymers of the present invention. Such packaging is prepared from the highly crystalline polymers which can be prepared using stereospecific catalysts. This packaging material has a low rate of water swellability such that it is suitable as packaging, but when disposed of, will slowly degrade to smaller units which would then be biodegradable. The packaging can be fabricated into the form of films or rigid containers.

The molecular weight of the polymers of the present invention can be selected as desired. Number average molecular weights of from 5,000 to 150,000 are typical. The particular molecular weight would be chosen depending upon the final end use and is readily determined by those skilled in the art.

The polymerization of the present invention can either be carried out in solution or in bulk. Suitable solvents for carrying out the polymerization of the solution include toluene, benzene, tetrahydrofuran, dimethyl sulfoxide, dimethyl formamide, acetonitrile, and other solvents in which the monomer is soluble. The temperature of polymerization is not particularly critical. At low temperatures the rate of polymerization will be slow while at more elevated temperatures, the rate of polymerization will proceed rapidly. Temperatures from 0° C. to in excess of 100° C. can be readily employed with temperatures of room temperature to 60° C. being preferred. The upper limit on the temperature is not critical, especially when using the racemic mixture of the malolactone ester or amide. However, when either the D or L form in substantially pure form is to be polymerized, care should be taken not to conduct the polymerization at temperatures at which either the pure D or pure L form is racemized.

As indicated previously, either acid or base polymerization initiators may be employed such as betaine, triethylamine, iron trichloride, triethylaluminum, $Et_4N^+Bz^-$ or other tetraalkylammonium carboxylate salts, zinc carbonate, basic zinc carbonate, diethylzinc, titanium, magnesium or barium compounds, litharage, stannous octoate and the like. Further, the polymerization process of U.S. Pat. No. 3,471,456 may also be employed.

After polymerization of the malolactone ester or amide it is possible to convert the ester or amide group to the free carboxylic acid group. When it is desired to produce polymers containing free carboxyl pendant groups, it is preferred to employ as the ester or amides radicals which may be readily removed under mild conditions so that the polymer backbone is not broken. Particularly preferred are the methyl and ethyl esters which may be hydrolyzed under very mild conditions and the benzyl ester which can be removed by hydrogenylosis of the ester polymer. The use of hydrogenylosis eliminates the possibility of the polymer backbone being degraded during the preparation of the free carboxyl groups.

The polymers produced by the present invention can be processed using conventional processing techniques to produce fibers, films and the like. If desired, the polymers of the present invention can be cross-linked using suitable cross-linking agents which will react with the pendant carboxyl groups, such as diols, triols and the like. Suitable procedures disclosed in U.S. Pat. Nos. 3,575,907, 3,297,033, 3,299,171 and 3,636,956 may be used to process these new polymers. The polymers wherein the pendant carboxyl group is protected with an ester, amide or similar moiety may be melt processed or solution processed. When the carboxyl group is the free acid it is generally preferred to process the polymer as a solution.

Having generally described this invention, a further understanding can be obtained by reference to certain specific examples which are provided herein for purposes of illustration only and are not intended to be limiting unless otherwise specified.

EXAMPLE 1

Synthesis of malolactonic acid benzyl ester (MLABE)

Bromosuccinic anhydride was prepared by refluxing 60 g of acetyl chloride containing 50 g (0.253 mole) of commercial bromosuccinic acid up to complete dissolution of the latter. After removing the excess acetyl chloride and the acetic acid formed by simple distillation, bromosuccinic anhydride (35 g) was vacuum distilled (93° C./0.3 mm Hg). To this collected bromosuccinic anhydride (0.195 mole), 21 g (0.195 mole) of benzyl alcohol was added. The mixture was allowed to stir overnight at room temperature to yield 56 g of a mixture of the two bromosuccinic acid monobenzyl ester isomers I and II. This crude mixture, placed in a 2 l three-necked flask equipped with a condenser, an efficient stirring system and a dropping funnel, was neutralized with 16.4 g of $NaHCO_3$ dissolved in 400 $cm^3$ of water. Then, 300 $cm^3$ of diethyl ether were added and then 100 $cm^3$ of a 2M $AgNO_3$ water solution was added slowly in 4 hours. The ethereal phase was separated, washed twice with water containing a small amount of $NaHCO_3$ and allowed to stand overnight in the presence of anhydrous sodium sulfate. After filtration and distillation of the solvent, the viscous residue was vacuum distilled twice on $CaH_2$ (95° C./0.005 mm Hg). At last, 6 g of malolactonic acid benzyl ester were obtained. (Elem. anal.: theor. C% = 64.05 H% = 4.85; found C% = 64.18, H% = 4.86).

Polymerization of MLABE:

MLABE was polymerized in capped vessels under dry nitrogen atmosphere using the self-sealing liner and the hypodermic technics in a glove-bag filled up with dry nitrogen. Reagents were added in the following order: solvent, catalyst or initiator, monomer. Mixtures were stirred at fixed temperature throughout the polymerization. Then, the solvent was evaporated (when present) and the residue was dissolved in acetone to make a 20% solution. A few drops of HCl were added and PMLABE's were precipitated by methanol (final composition: 80/20-V/V-methanol/acetone). The process was repeated once under the same conditions but in the presence of HCl. At last, the product was dried in a vacuum oven at 50° C. The results are reported in Table I.

Removal of benzyl protective groups from PMLABE

PMLABE (1.935 g, run n°3) was dissolved in 15 cm³ of ethyl acetate. Then, 15 cm³ of ethyl alcohol and 400 mg of 10% Pd on charcoal were added. The flask was connected to a volumetric tank. After purging, the hydrogenation device was filled up with hydrogen at the atmospheric pressure and a regular stirring was started. The consumption of hydrogen was measured and standarize to normal temperature and pressure conditions. Samples of 2 cm³ (120 mg of polymer) were removed from the reaction medium at different times in order to follow the progress of the hydrogenation reaction by IR spectrometry.

pound to be treated, the cleavage proceeded progressively and quantitatively.

After 40 minutes, no further hydrogen was absorbed, indicating that the theoretical hydrogen uptake was reached for a total removal of all the protecting groups. Poly-β-malic acid was then isolated as a highly hygroscopic white powder after filtration of the catalyst and vacuum evaporation of the solvents.

Having now fully described this invention, it will be apparent to one of ordinary skill in the art that many changes and modifications can be made thereto without departing from the spirit or scope of the invention set forth herein.

What is claimed as new and intended to be covered by letters patent is:

1. A polymer containing repeating units of the formula:

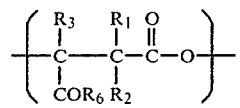

wherein $R_1$ and $R_2$ are independently hydrogen, alkyl, aryl, aralkyl, substituted alkyl, substituted aryl, substituted aralkyl, $R_3$ is hydrogen, alkyl or $-(CH_2)_n COOR_8$ where n is an integer of 0 to 10, $R_6$ is OR or $NR_4R_5$, wherein R and $R_8$ are independently hydrogen or a group derived from a compound containing esterifiable hydroxyl groups, $R_4$ and $R_5$ are independently alkyl, aryl, aralkyl, substituted alkyl, substituted aryl, substituted aralkyl or together comprise an alkylene group.

2. The polymer of claim 1, wherein $R_1$, $R_2$ and $R_3$ are hydrogen and $R_6$ is OR where R is benzyl, methyl or ethyl.

3. The polymer of claim 1, wherein $R_3$ is methyl and $R_1$ and $R_2$ are hydrogen and $R_6$ is OR where R is benzyl,

TABLE 1

POLYMERIZATION OF MALOLACTONIC ACID BENZYL ESTER (MLABE) BY USING DIFFERENT INITIATOR OR CATALYST SYSTEMS

| Run n° | (M) mole . l$^{-1}$ | Initiator \or catalyst | (I) (M) | Polymerization$^c$ temp °C. | time days | conv. % | Yield$^{(d)}$ % | $\overline{M}^{(f)}$ GPC | (g) $M_p$°C. |
|---|---|---|---|---|---|---|---|---|---|
| 1 | bulk | Betaine$^{(b)}$ | $10^{-3}$ | 60 | 3 | 100 | 30 | $2.5 \times 10^{-3}$ | — |
| 2 | bulk | N Et$_3$ | $10^{-3}$ | RT | 21 | 65 | 40 | $7 \times 10^{-3}$ | 79 |
| 3 | bulk | Betaine$^{(b)}$ | $10^{-3}$ | RT | 21 | 80 | 55 | $7 \times 10^{-3}$ | 80 |
| 4 | bulk | tetraethyl-ammonium benzoate | $10^{-3}$ | 50 | 7 | 40 | 20 | $2 \times 10^{-3}$ | — |
| 5 | 2.5 (toluene) | FeCl$_3$ | $10^{-2}$ | 50 | 7 | — | 30 | — | 76 |
| 6 | 2.5 (toluene) | AlEt$_3$ | $10^{-2}$ | 50 | 7 | — | 10$^{(e)}$ | — | 165–185 |

$^{(a)}$crude monomer before vacuum distillation
$^{(b)}$Me$_3$N$^+$—CH$_2$—COO from dried betaine monohydrate
$^{(c)}$deduced from Ir of the reaction mixture (lactone C=O at 1855 cm$^{-1}$)
$^{(d)}$calculated from the polymer isolated after two precipitations
$^{(e)}$fraction insoluble in acetone
$^{(f)}$based on polystyrene standards
$^{(g)}$from endothermic peaks observed in DSC

EXAMPLE 2

Side chain benzyl ester groups of a sample of PMLABE (run 3 in Table I) were selectively cleaved to the corresponding free carboxylic acid compounds by using catalytic hydrogenolysis.

The hydrogenation was carried out at room temperature in a 50/50 ethyl acetate/ethanol solvent mixture. Despite the polymeric character of the organic commethyl or ethyl.

4. The polymer of claim 1, wherein $R_1$ and $R_2$ are hydrogen and $R_3$ is $-(CH_2)_n COOR_8$.

5. The polymer of claim 4, wherein R is methyl.

6. The polymer of claim 1, wherein repeating units derived from lactones, cyclic esters, lactams or cyclic amides are present.

7. The polymer of claim 1, wherein repeating units derived from caprolactam are present.

8. The polymer of claims 2, 3 or 4 wherein R is benzyl.

9. A copolymer obtained by copolymerizing caprolactam or caprolactone with a monomer having the formula:

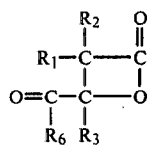

wherein $R_1$, $R_2$, $R_3$ and $R_6$ are as defined in claim 1.

10. The copolymer of claim 9, wherein $R_6$ is converted to a hydroxyl group after polymerization.

11. A suture prepared from the polymer of claim 1, wherein $R_1$, $R_2$ and $R_3$ are hydrogen.

12. A suture prepared from the polymer of claim 1, wherein $R_1$ and $R_2$ are hydrogen and $R_3$ is methyl.

13. A suture prepared from the polymer of claim 1, wherein $R_1$ and $R_2$ are hydrogen and $R_3$ is $-(CH_2)-COOR_8$.

14. A fiber prepared from the polymer of claim 1.

15. A fiber prepared from the polymer of claim 10.

16. Biodegradable packaging prepared from the polymer of claim 1.

* * * * *

UNITED STATES PATENT AND TRADEMARK OFFICE
CERTIFICATE OF CORRECTION

PATENT NO. : 4,265,247

DATED : May 5, 1981

INVENTOR(S) : Robert W. Lenz et al.

It is certified that error appears in the above—identified patent and that said Letters Patent is hereby corrected as shown below:

Column 7, Table 1, ninth column from the left, delete the numbers in the first four lines of data and insert in lieu thereof the following numbers:

$$-- \quad 2.5 \times 10^3$$
$$7 \times 10^3$$
$$7 \times 10^3$$
$$2 \times 10^3$$

Signed and Sealed this

Fifth Day of January 1982

[SEAL]

Attest:

GERALD J. MOSSINGHOFF

*Attesting Officer*  *Commissioner of Patents and Trademarks*